United States Patent
Gliner et al.

(10) Patent No.: US 10,578,737 B2
(45) Date of Patent: Mar. 3, 2020

(54) USING PROXIMAL LOCATION SENSORS TO IMPROVE ACCURACY AND LOCATION IMMUNITY TO INTERFERENCE

(71) Applicant: Biosense Webster (Israel) Ltd., Yokneam (IL)

(72) Inventors: Vadim Gliner, Haifa (IL); Assaf Govari, Haifa (IL); Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 136 days.

(21) Appl. No.: 15/599,942

(22) Filed: May 19, 2017

(65) Prior Publication Data
US 2018/0335519 A1    Nov. 22, 2018

(51) Int. Cl.
| | |
|---|---|
| *G01S 17/06* | (2006.01) |
| *G01S 17/89* | (2006.01) |
| *G01S 7/497* | (2006.01) |
| *G01S 17/42* | (2006.01) |
| *A61B 5/06* | (2006.01) |
| *A61B 5/00* | (2006.01) |
| *A61B 5/1495* | (2006.01) |
| *G01S 7/481* | (2006.01) |

(52) U.S. Cl.
CPC ............ *G01S 17/06* (2013.01); *A61B 5/062* (2013.01); *A61B 5/1495* (2013.01); *A61B 5/6852* (2013.01); *A61B 5/742* (2013.01); *G01S 7/497* (2013.01); *G01S 17/42* (2013.01); *G01S 17/89* (2013.01); *A61B 2562/043* (2013.01); *G01S 7/4817* (2013.01)

(58) Field of Classification Search
CPC . A61B 2562/043; A61B 5/062; A61B 5/1495; A61B 5/6852; A61B 5/742; G01S 17/06; G01S 17/42; G01S 17/89; G01S 7/4817; G01S 7/497
USPC ......................... 702/150; 600/424, 513, 11
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron |
| (Continued) | | |

FOREIGN PATENT DOCUMENTS

| | | |
|---|---|---|
| EP | 1174082 A1 | 1/2002 |
| EP | 1181891 A2 | 2/2002 |
| WO | 199605768 A1 | 2/1996 |

OTHER PUBLICATIONS

Extended European Search Report dated Aug. 7, 2018 for the European Patent Application No. 18173228.0.

*Primary Examiner* — John H Le
(74) *Attorney, Agent, or Firm* — Volpe and Koenig, P.C.

(57) ABSTRACT

A system and method for determining location of a tool having a distal end sensor and at least one other sensor is presented. The method includes obtaining data from the distal end sensor, performing convergence on the obtained data, the convergence indicating whether or not the obtained data is disturbed, when the convergence indicates the obtained data is not disturbed, calculate the location of the tool using the obtained data, and when the convergence indicates the obtained data is disturbed, obtaining additional data from the at least one other sensor, performing the convergence on the obtained additional data, and calculating the location of the tool using the obtained additional data.

19 Claims, 4 Drawing Sheets

(56) References Cited

U.S. PATENT DOCUMENTS

| | | |
|---|---|---|
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben-Haim |
| 2002/0065455 A1 | 5/2002 | Ben-Haim |
| 2003/0120150 A1 | 6/2003 | Govari |
| 2004/0068178 A1 | 4/2004 | Govari |
| 2004/0210121 A1 | 10/2004 | Fuimaono |
| 2007/0078334 A1 | 4/2007 | Scully |
| 2009/0138007 A1 | 5/2009 | Govari |
| 2011/0237933 A1* | 9/2011 | Cohen .................... A61B 5/062 600/424 |
| 2012/0149967 A1 | 6/2012 | Ludwin |

* cited by examiner

USING PROXIMAL LOCATION SENSORS TO IMPROVE ACCURACY AND LOCATION IMMUNITY TO INTERFERENCE

SUMMARY

A system and method for determining the location of a tool having a distal end sensor and at least one other sensor is presented. In one embodiment, the method can perform steps of obtaining data from the distal end sensor, performing convergence on the obtained data, the convergence indicating whether or not the obtained data is disturbed, when the convergence indicates the obtained data is not disturbed, calculating the location of the tool using the obtained data, and when the convergence indicates the obtained data is disturbed, obtaining additional data from the at least one other sensor, performing the convergence on the obtained additional data, and calculating the location of the tool using the obtained additional data.

In one embodiment, the method can also calculate a difference between the obtained data and an actual magnetic field at a same location. In one embodiment, the method can also determine that convergence is indicated when the difference is less than a predetermined threshold. In one embodiment, the method can also display the location of the tool on a display screen.

In one embodiment, the method can also obtain, from another tool, a magnetic field interfering with the obtained data. In one embodiment, the obtained data is magnetic field data.

The system for determining location of a tool having a distal end sensor and at least one other sensor can comprise a display device and a processor configured to obtain data from the distal end sensor, perform convergence on the obtained data, the convergence indicating whether or not the obtained data is disturbed, when the convergence indicates the obtained data is not disturbed, calculate the location of the tool using the obtained data, and when the convergence indicates the obtained data is disturbed, obtain additional data from the at least one other sensor, perform the convergence on the obtained additional data, and calculate the location of the tool using the obtained additional data.

In one embodiment, the system can also calculate a difference between the obtained data and an actual magnetic field at a same location. In one embodiment, the system can also determine that convergence is indicated when the difference is less than a predetermined threshold. In one embodiment, the system can further comprise a display device such as a display screen or monitor that can display the location of the tool.

In one embodiment, the system can further comprise another tool and the processor is further configured to obtain, from the other tool, a magnetic field interfering with the obtained data. In one embodiment, the obtained data is magnetic field data.

A computer program product for using proximal location sensors to improve accuracy and location immunity to interference is also presented.

BRIEF DESCRIPTION OF THE DRAWINGS

A more detailed understanding can be had from the following description, given by way of example in conjunction with the accompanying drawings wherein.

DETAILED DESCRIPTION

Magnetic navigation systems used for navigating tools, such as medical implements, catheters, wireless devices, wired devices, etc., generally comprise coils with magnetic fields, and each coil has its own frequency. Also, the systems include one or more sensors in space, each sensor typically receiving all coil frequencies. Since each coil has a unique frequency with respect to other coils, the sensor can tell which coil is where. Magnetic systems are typically quite accurate for the navigation of a particular tool, but the systems are very susceptible to interference from other magnetic elements and/or devices. For example, if a second magnetic tool is activated or used, different from the particular (first) tool being navigated by the system, interference is generated by this second tool. In other words, if one is navigating a first tool with a sensor and a second tool is introduced near the first tool, the second tool's magnetic field(s) interfere with the first tool's, causing the first tool to have inaccurate readings. Such interference and inaccurate readings are a problem because they disrupt the first tool's navigation. Thus, while the first tool's location can be calculated, that first tool's calculated location is not valid; the first tool is "disturbed" by interference from another magnetic field, so that the correct location of the first tool is not known. Instead, it is only known that there is interference.

One such magnetic navigation system can be found in CARTO™, produced by Biosense Webster, Inc. (Diamond Bar, Calif.). In magnetic navigation systems, magnetic fields are typically generated by a location pad consisting of field generators. In a magnetic navigation system, magnetic position sensing may be used to determine position coordinates of distal end of a tool inside a patient's organ. For this purpose, a driver circuit in a console or a location pad drives field generators to generate magnetic fields within the body of patient. Typically, the field generators comprise coils, which are placed beneath the patient's body at known positions external to the patient. These coils generate magnetic fields in a predefined working volume that contains the patient's organ to be explored. A magnetic field sensor within distal end of the tool generates electrical signals in response to these magnetic fields. A signal processor processes these signals in order to determine the position coordinates of the distal end, typically including both location and orientation coordinates. This method of position sensing is implemented in the above-mentioned CARTO™ system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

During a procedure using a particular tool, for example a catheter, with a magnetic navigation system, the location of the catheter's distal sensor is typically determined by measuring the main magnetic field enabled in the navigation system. These magnetic field measurements are typically sensed by the distal sensor of the particular tool, convergence is performed on the sensed measurements and the location, e.g., position and orientation, of the tool is determined since the tool is rigid and the location of the distal sensor relative to the tool is known. In magnetic navigation systems, magnetic fields are typically generated by a location pad consisting of field generators. Each field generator emits a field in a specific frequency. In one embodiment, a location field generated by the field generators of the location pad emits fifteen (15) frequencies.

However, the distal sensor may have difficulty receiving data due to, for example, metal interference. Any metallic object or element, or any group of metallic objects can cause interference and/or can cause a sensor to become intolerant, e.g., cause the sensor to provide inaccurate data. When the data at the distal sensor does not converge, the location of the distal sensor is difficult to determine, making navigation of the catheter difficult.

An inventive solution that overcomes the interference problem and the intolerance of the distal sensor is presented. In this inventive system, two or more additional, proximal sensors can be placed on the tool, e.g., a catheter tube; these sensors, in addition to the distal sensor, can measure the strength of the main magnetic field. When the location of the distal sensor does not converge, one or more of the additional, proximal sensors can be used to determine the tool's location to enable more accurate navigation. In particular, whether the proximal sensors converge better than the distal sensor can be checked. If the proximal sensors converge better, this indicates that the distal sensor suffers from magnetic disturbance (otherwise it would perfectly converge). As discussed below, convergence is a "grade" or numerical value that can be compared to a threshold, for example, to determine how close one converges to the theoretical field.

Accordingly, the system detects when there is magnetic interference from a specific sensor (for example a distal sensor), and selects one or more of the other sensors (for example a proximal sensor) to take accurate measurements. Accordingly, the inventive system comprises multiple sensors on a tool and is able to test convergence and switch to a sensor that is not subject to interference. In one embodiment, convergence is tested as calculation of root means square error (RMSE) of the value of received fields minus the value of those fields that are assumed, based on calibration, to be in the specific point or location.

In one embodiment, the data can also be retrofitted. In one embodiment, convergence of at least nine (9) readings indicates the location of the catheter, where each of the nine readings is from a different frequency. More or fewer than 9 readings can be used. Since typically more than 9 readings are available, one can test additional readings to determine whether one or more of these additional magnetic fields fits the specific location. If so, the location can be successfully determined. If not enough of the additional readings combined with the initial readings fit the magnetic location, the field is considered to be disturbed, that is, to have interference. In one embodiment, at least 9 readings are needed for convergence. Typically, convergence is performed by collecting data from multiple sensors and determining whether this data tends to come together or tends to meet at a particular point. In one embodiment, the conjugate gradient method is used as a convergence algorithm.

An inventive solution that overcomes the interference problem and the intolerance of the distal sensor is presented. In this inventive system, two or more additional, proximal sensors can be placed on the tool, e.g., a catheter tube; these sensors, in addition to the distal sensor, can measure the strength of the main magnetic field. When the location of the distal sensor does not converge, one or more of the additional, proximal sensors can be used to determine the tool's location to enable more accurate navigation. Accordingly, the system detects when there is magnetic interference from a specific sensor (for example a distal sensor), and selects one or more of the other sensors (for example a proximal sensor) to take accurate measurements. Accordingly, the inventive system comprises multiple sensors on a tool and is able to test convergence and switch to a sensor that is not subject to interference. In one embodiment, convergence is tested as calculation of root means square error (RMSE) of the value of received fields minus the value of those fields that are assumed, based on calibration, to be in the specific point or location.

Figure 1:
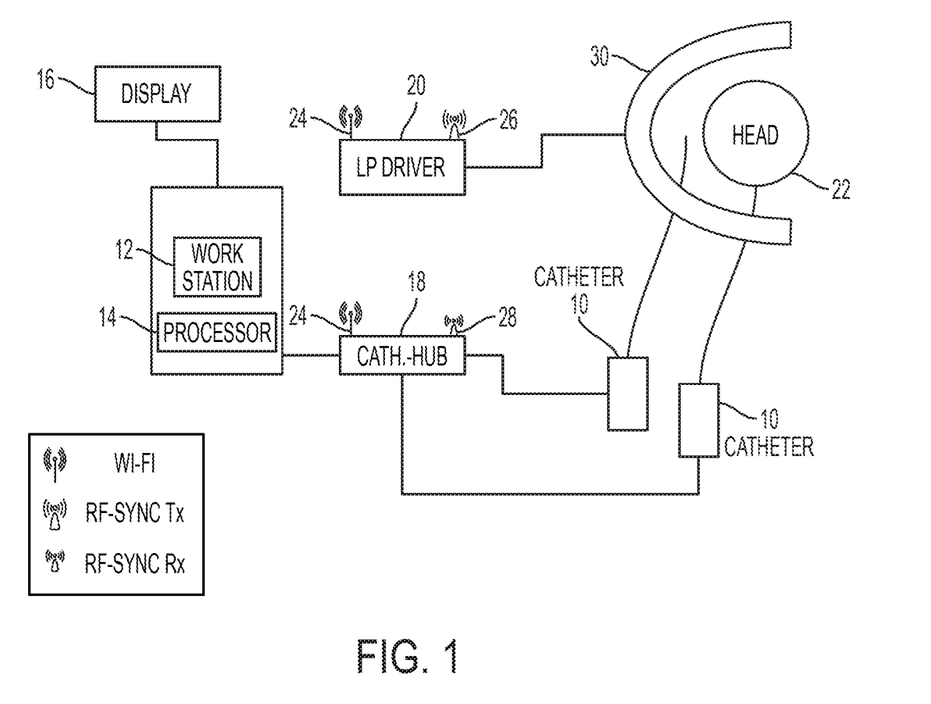
FIG. 1 is a schematic overview of the system in accordance with an embodiment of the present invention.

FIG. 1 is a schematic overview of the system in accordance with an embodiment of the present invention. As shown in FIG. 1, the system can comprise a medical tool 10 (e.g., catheter, catheter tube, etc.), a work station 12 comprising at least a processor 14 and a display or monitor 16, a catheter hub 18, an LP driver 20, a patient (only head is shown) 22, WiFi antenna 24, RF Sync Tx antenna 26, RF Sync Rx antenna 28 and location pad 30. The medical tool 10 can be either wired or wireless. In one embodiment, the catheter hub 18 receives data from all of the sensors 32, 34, 36 that are navigated, and the LP driver 20 drives current to the location pad 30, the current enabling the field generators to generate magnetic fields. In one embodiment, the catheter hub 18 comprises a WiFi antenna 24 and an RF Sync Rx antenna 28, for receiving signals from the tools that are navigated. In one embodiment, the LP driver 20 comprises a WiFi antenna 24 and an RF Sync Tx antenna 26 enabling the LP driver 20 to transmit current to the location pad 30.

The position and orientation of the distal end of the tool 10 may be ascertained by determining the position of the magnetic field locating sensor 32, 34, 36. The tool 10 may be locatable with a non-ionizing field, such as an electromagnetic or acoustic field. As discussed above, the tip of the tool 10 may comprise a transmitting or receiving antenna (not shown) for the relevant field. Receiving or transmitting antennas (not shown) for the non-ionizing field are attached to a patient; to be examined. A receiver or transmitter is connected to these antennas, and converts the received field waves into electrical locating or image signals.

The location pad 30 may comprise coils (not shown), which are one type of magnetic transducer that may be used in embodiments of the present invention. A "magnetic transducer," in the context of the present patent application and in the claims, means a device that generates a magnetic field in response to an applied electrical current and/or outputs an electrical signal in response to an applied magnetic field. Although the embodiments described herein use coils as magnetic transducers, other types of magnetic transducers may be used in alternative embodiments, as will be apparent to those skilled in the art.

The work station 12 can be detachably connected to the display 16. The work station 12 is also detachably connected to the catheter hub 18 to which one or more medical tools 10 can be connected. The connections can be hard-wired or WiFi connections, or both. The tool 10, such as a catheter or ENT tool, can be navigated through the patient's head 22. Although the work station 12, the LP driver 20 and the catheter hub 18 are shown as separate components, they may all be separate components, they may all be included together in a single component, or variously combined as fewer components.

Figure 2:
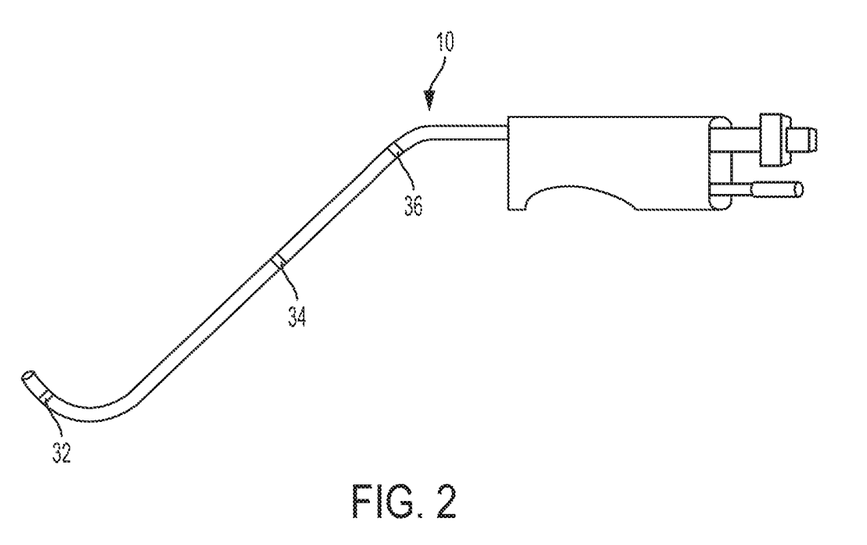
FIG. 2 is a sectional view of the distal end of a tool, in accordance with an embodiment of the present invention.

FIG. 2 is sectional view of the distal end of a tool 10, in accordance with an embodiment of the present invention. As shown in FIG. 2, the tool 10 has multiple sensors 32, 34, 36 (while three sensors are shown, more or fewer than three sensors can be used). Each sensor can receive signals from coils in the location pad 30. One or more of the coils may also be used to output signals in response to the magnetic fields generated by field generators, typically located in the location pad 30, and thus serve as position sensing coils. Processor 14 processes these signals in order to determine the coordinates (position and orientation) of the distal end of the tool 10 in the external frame of reference that is defined by the field generators.

In one embodiment, processor 14 receives the signal data generated by the sensors 32, 34, 36 on the tool 10 via the catheter hub 18. Processor 14 processes these signal data in order to determine the location of the tool 10. The processing can include analysis of calculating convergence, as mentioned above. In one embodiment, convergence can be found when the difference between the calibrated magnetic field at a particular location and the actual magnetic field (e.g., in Gauss/Ampere) at the same location is less than a predetermined threshold. For example, the equation ||B_calibration−B_actual||<Threshold may be used to determine convergence. The result of the convergence calculation is the calculated location of the distal end of the tool 10.

The present invention may be applied in applications that require accurate locating of a tool within a body, and particularly in therapeutic and diagnostic applications that use invasive probes, both in the heart and in other organs of the body. As one example, the devices and techniques for position and pressure sensing that are implemented in the inventive system may be applied in guiding and controlling the use of a catheter insertion sheath. If the position of the sheath is not properly controlled and excessive force is used in its insertion, the sheath may perforate the heart wall or vascular tissue. This eventuality can be avoided by sensing the position of and pressure on the distal tip of the sheath. In this regard, the term "distal tip" as used herein should be understood to include any sort of structure at the distal end of a probe that may be bent and/or displaced relative to the main body of the probe.

Figure 3:
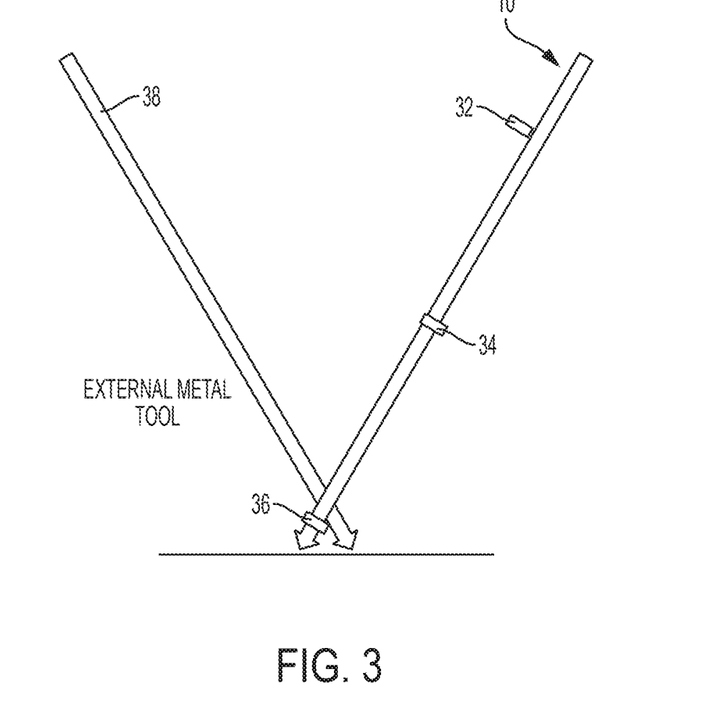
FIG. 3 is a schematic view of a tool, in accordance with another embodiment of the present invention, in the presence of a metal object.

FIG. 3 is a schematic view of a tool 10 in the presence of a metal object, such as an external metal tool 38. As discussed above, the interference caused by this object 38 is noticeable when it comes in close proximity to the distal end of the tool 10. To overcome this interference, data from proximal sensors 34 and 36 can be used to calculate convergence. Moreover, data from sensor 32, the distal end sensor, can be ignored. As mentioned above, the result of the convergence calculation is the calculated location of the distal end of the tool 10. This calculation initially is performed with data from the distal end sensor 32; however, when interference is determined at the distal end sensor 32, the convergence calculation is performed with data from other sensors 34, 36 on the tool 10.

Figure 4:
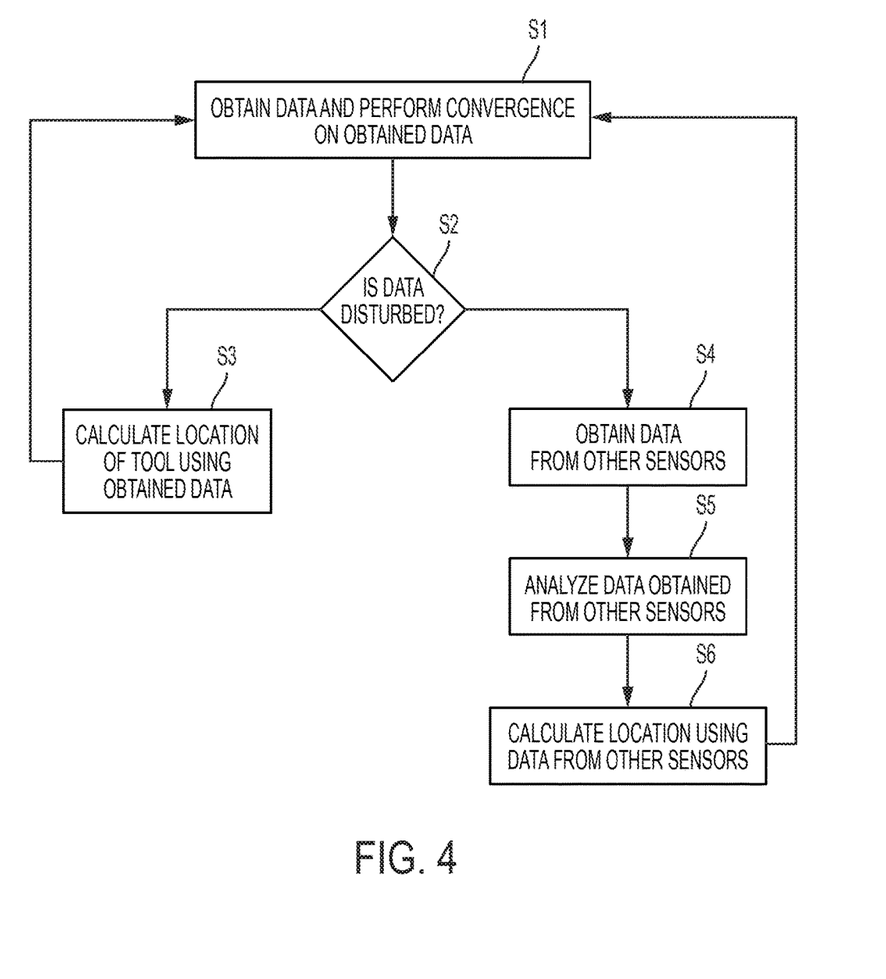
FIG. 4 is a flow diagram of the inventive method.

FIG. 4 is a flow diagram of the inventive method. In one embodiment, the method can proceed as follows. In step S1, obtain data from distal end sensor 32 of a tool 10; perform convergence algorithm with this obtained data.

In step S2, determine whether this obtained data (for example, from distal end sensor 32) is disturbed, e.g., has interference. If data from distal end sensor 32 is NOT disturbed (S2=NO), in step S3, use the obtained data to calculate the location of tool 10. Continue processing at step S1.

If data from distal end sensor 32 is disturbed (S2=YES), in step S4, obtain data from other sensors 34, 36 on tool 10. In step S5, analyze data obtained from the other sensors 34, 36, and perform the convergence algorithm with data from the non-distal end (non-disturbed) sensors. In step S6, calculate the location of the tool 10 using additional data from the non-distal end sensor(s).

It should be understood that many variations are possible based on the disclosure herein. Although features and elements are described above in particular combinations, each feature or element can be used alone without the other features and elements or in various combinations with or without other features and elements.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements method described herein.

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method for locating a tool in a three dimensional (3D) space which improves processing performance, comprising:
   obtaining, from a first sensor disposed at the tool, a plurality of first data each generated in response to receiving one of a plurality of magnetic fields at a location of the first sensor;
   determining whether the plurality of first data converges at the location of the first sensor;
   when the plurality of first data is determined to converge at the location of the first sensor, calculating a location of the tool to be displayed using the plurality of first data; and
   when the plurality of first data is determined not to converge at the location of the first sensor:
      obtaining, from at least one other sensor disposed at a second portion of the tool spaced from the first sensor, a plurality of second data each generated in response to receiving one of the plurality of magnetic fields at a location of the at least one other sensor; and
      calculating the location of the tool to be displayed using the plurality of second data.

2. The method according to claim 1, wherein determining whether the plurality of first data converges at the location of the first sensor further comprises:

calculating a difference between values of the magnetic fields indicated by the plurality of first data and predetermined magnetic field values at the location of the first sensor.

3. The method according to claim 2, wherein the plurality of first data is determined to converge at the location of the first sensor if the difference is less than a predetermined threshold.

4. The method according to claim 1, further comprising receiving each of the plurality of magnetic fields from one of a plurality of magnetic field generators at different locations,
wherein each of the plurality of magnetic fields comprising a different frequency.

5. The method according to claim 1, wherein determining whether the plurality of first data converges at the location of the first sensor comprises calculating a difference between a root means square error (RMSE) of values of each of the plurality of data and predetermined magnetic field values at the location of the first sensor.

6. The method according to claim 1, wherein the first sensor is disposed at a distal end of the tool and the at least one other sensor is disposed at a proximal end of the tool.

7. A system for locating a tool in a three dimensional (3D) space which improves processing performance, the system comprising:
a display device; and
a processor configured to:
obtain, from a first sensor disposed at the tool, a plurality of first data each generated in response to receiving one of a plurality of magnetic fields at a location of the first sensor;
determining whether the plurality of first data converges at the location of the first sensor;
when the plurality of first data is determined to converge at the location of the first sensor, calculate a location of the tool to be displayed using the plurality of first data; and
when the plurality of first data is determined not to converge at the location of the first sensor:
obtain, from at least one other sensor disposed at a second portion of the tool spaced from the first sensor, a plurality of second data each generated in response to receiving one of the plurality of magnetic fields at a location of the at least one other sensor; and
calculate the location of the tool to be displayed using the plurality of second data.

8. The system according to claim 7, wherein the processor is further configured to:
determine whether the plurality of first data converges at the location of the first sensor by calculating a difference between values of the magnetic fields indicated by the plurality of first data and predetermined magnetic field values at the location of the first sensor.

9. The system according to claim 8, wherein the processor is further configured to:
determine that the plurality of first data converges at the location of the first sensor if the difference is less than a predetermined threshold.

10. The system according to claim 7, further comprising a display screen and the processor is further configured to display the location of the tool on the display screen.

11. The system according to claim 7, wherein the processor is further configured to receive each of the plurality of magnetic fields from one of a plurality of magnetic field generators at different locations,
wherein each of the plurality of magnetic fields comprising a different frequency.

12. The system according to claim 7, wherein the processor is further configured to determine whether the plurality of first data converges at the location of the first sensor by calculating a difference between a root means square error (RMSE) of values of each of the plurality of data and predetermined magnetic field values at the location of the first sensor.

13. The system according to claim 7, wherein the first sensor is disposed at a distal end of the tool and the at least one other sensor is disposed at a proximal end of the tool.

14. A non-transitory computer readable storage medium in which computer program instructions are stored, which instructions, when executed by a computer, cause the computer to execute a method of locating a tool in a three dimensional (3D) space comprising:
obtaining from a first sensor disposed at the tool, a plurality of first data each generated in response to receiving one of a plurality of magnetic fields at a location of the first sensor;
determining whether the plurality of first data converges at the location of the first sensor;
when the plurality of first data is determined to converge at the location of the first sensor, calculating a location of the tool to be displayed using the plurality of first data; and
when the plurality of first data is determined not to converge at the location of the first sensor:
obtaining, from at least one other sensor disposed at a second portion of the tool spaced from the first sensor, a plurality of second data each generated in response to receiving one of the plurality of magnetic fields at a location of the at least one other sensor; and
calculating the location of the tool to be displayed using the plurality of second data.

15. The computer readable storage medium according to claim 14,
wherein determining whether the plurality of first data converges at the location of the first sensor further comprises calculating a difference between values of the magnetic fields indicated by the plurality of first data and predetermined magnetic field values at the location of the first sensor.

16. The computer readable storage medium according to claim 15,
wherein the plurality of first data is determined to converge at the location of the first sensor if the difference is less than a predetermined threshold.

17. The computer readable storage medium according to claim 14, further comprising:
displaying the location of the tool on a display screen.

18. The computer readable storage medium according to claim 14, further comprising receiving each of the plurality of magnetic fields from one of a plurality of magnetic field generators at different locations,
wherein each of the plurality of magnetic fields comprising a different frequency.

19. The computer readable storage medium according to claim 14, wherein determining whether the plurality of first data converges at the location of the first sensor comprises calculating a difference between a root means square error (RMSE) of values of each of the plurality of data and predetermined magnetic field values at the location of the first sensor.

* * * * *

UNITED STATES PATENT AND TRADEMARK OFFICE
CERTIFICATE OF CORRECTION

PATENT NO. : 10,578,737 B2
APPLICATION NO. : 15/599942
DATED : March 3, 2020
INVENTOR(S) : Vadim Gliner et al.

It is certified that error appears in the above-identified patent and that said Letters Patent is hereby corrected as shown below:

In the Drawings
In Fig. 4, Sheet 4 of 4, for Tag "S1", in Line 1, delete "DATAAND" and insert -- DATA AND --, therefor.

In the Specification
In Column 4, Line 41, delete "patient;" and insert -- patient --, therefor.
In Column 4, Line 66, delete "is sectional" and insert -- is a sectional --, therefor.

Signed and Sealed this
Twenty-fourth Day of January, 2023

Katherine Kelly Vidal
*Director of the United States Patent and Trademark Office*